United States Patent
Tai et al.

(10) Patent No.: US 6,638,709 B2
(45) Date of Patent: Oct. 28, 2003

(54) PROCESSES FOR MAKING CRYOPRESERVED COMPOSITE LIVING CONSTRUCTS AND PRODUCTS RESULTING THEREFROM

(75) Inventors: Hsin-Chien Tai, Hackensack, NJ (US); Alla Laufer, Brooklyn, NY (US); Ying Song, Franklin Park, NJ (US); Nitya G. Ray, East Hanover, NJ (US)

(73) Assignee: Ortec International, Inc., New York, NY (US)

( * ) Notice: Subject to any disclaimer, the term of this patent is extended or adjusted under 35 U.S.C. 154(b) by 81 days.

(21) Appl. No.: 10/032,929

(22) Filed: Dec. 26, 2001

(65) Prior Publication Data

US 2002/0123809 A1 Sep. 5, 2002

Related U.S. Application Data

(60) Provisional application No. 60/258,009, filed on Dec. 27, 2000.

(51) Int. Cl.$^7$ .............................. A01N 1/02; A01N 1/00
(52) U.S. Cl. ..................................... 435/1.3; 623/23.72
(58) Field of Search .................. 435/1.3, 347, 374; 623/23.72, 915, 920

(56) References Cited

U.S. PATENT DOCUMENTS

| | | | |
|---|---|---|---|
| 3,842,831 A | 10/1974 | Beisang et al. | 128/155 |
| 4,890,457 A | 1/1990 | McNally et al. | 62/65 |
| 5,122,110 A | 6/1992 | McNally et al. | 600/36 |

(List continued on next page.)

FOREIGN PATENT DOCUMENTS

| EP | 0296475 B1 | 8/1992 |
|---|---|---|
| EP | 0532670 B1 | 3/1998 |

OTHER PUBLICATIONS

Ashwood–Smith, et al.; *Low–Temperature Preservation of Mammalian Cells in Tissue Culture with Polyvinylpyrrolidone (PVP), Dextrans, and Hydroxyethyl Starch (HES)*, Cryobiology 9; 441–449, 1972.

(List continued on next page.)

*Primary Examiner*—Corrine McDermott
*Assistant Examiner*—Will H Matthews
(74) *Attorney, Agent, or Firm*—Ralph T. Lilore

(57) ABSTRACT

Processes are described for making a cryopreserved Composite Living Construct (CCLC) as well as a corresponding thawed and rinsed CCLC, comprised of separated layers of cultured fibroblasts and cultured keratinocytes, wherein the percent of cells that are viable, i.e., the cell viability, of such CCLC is at least about 70 %. The viable cell density in the CCLC is at least about 50% of that before cryopreservation. The storage stability of the CCLC is at least about 12 months. Additionally, the metabolic activity of thawed and rinsed CCLC is at least about 50% of the Composite Living Construct (CLC) before cryopreservation. The structural integrity of CCLC is substantially the same as the CLC before cryopreservation. The process for making the CCLC comprises the steps of: providing a collagen substrate comprised of a collagen sponge layer and a nonporous to cells, semipermeable collagen layer; seeding and culturing, in the presence of a cell growth medium, fibroblasts on and within the collagen sponge layer and keratinocytes on the nonporous to cells, semipermeable collagen layer, thereby providing a CLC; equilibrating the CLC, according to a defined equilibration program with a cryoprotectant solution comprising at least chondroitin sulfate and dimethylsulfoxide; lowering the temperature, according to a programmed rate, to about –90° C.; and storing the CCLC at about –150° C. or lower. The process for preparing the CCLC to treat wounds in humans and in animals additionally comprises programmed thawing as well as a rinsing sequence to substantially remove the cryoprotectants.

10 Claims, 4 Drawing Sheets

U.S. PATENT DOCUMENTS

| | | | |
|---|---|---|---|
| 5,145,769 A | 9/1992 | McNally et al. | 435/1 |
| 5,145,770 A | 9/1992 | Tubo et al. | 435/1 |
| 5,149,621 A | 9/1992 | McNally et al. | 435/1 |
| 5,158,867 A * | 10/1992 | McNally et al. | 435/1.3 |
| 5,160,313 A | 11/1992 | Carpenter et al. | 600/36 |
| 5,298,417 A | 3/1994 | Cancedda et al. | 435/240.1 |
| 5,328,821 A | 7/1994 | Fisher et al. | 435/1 |
| 5,518,878 A | 5/1996 | Wilkins et al. | 435/1.3 |
| 5,891,617 A | 4/1999 | Watson et al. | 435/1.3 |
| 5,964,096 A | 10/1999 | Watson et al. | 62/78 |
| 6,136,525 A * | 10/2000 | Mullon et al. | 435/1.3 |
| 6,167,089 A * | 12/2000 | Boyce et al. | 375/240.15 |

OTHER PUBLICATIONS

Blondet, et al.; *Skin Preservation by Programmed Freezing,* Brit. Jrnl of Plastic Surgery, 35; 530–536, 1982.

Fahy, et al.; *Vitrification as an Approach to Cryopreservation,* Cryobiology 21; 407–426, 1984.

Kearney, et al.; *Effects of Cryobiological Variables on the Survival of Skin Using a Defined Murine Model,* Cryobiology 27; 164–170, 1990.

Teasdale, et al.; *Cryopreservation of Cultured Dermal Fibroblast Impregnated Collagen Gels,* Burns 19; (5), 406–410, 1993.

Karlsson, et al.; *Long–Term Storage of Tissues by Cryopreservation: Critical Issues,* Biomaterials 17; (3), 243–256, 1996.

Zieger, et al.; *Mechanisms of Cryoinjury and Cryoprotection in Split–Thickness Skin,* Cryobiology 33; 376–389, 1996.

Orton–Applegate et al.; *Engineering Aspects of the Cryopreservation of a Cultured Metabolically Active Human Dermal Replacement,* Cryobiology, 33 (6), 679, 1996.

de Kanter, et al.; *A Rapid and Simple Method For Cryopreservation of Human Liver Slices,* Xenobiotica 28 (3); 225–234, 1998.

Udoh et al.; *Long Term Viability of Cryopreserved Cultured Epithelial Grafts,* Burns, 26 (6), 535–542, Sep. 2000.

Liu et al.; *Comparison of the Stress Response to Cryopreservation in Monolayer & Three Dimensional Human fibroblast Cultures: Stress Proteins, MAP Kinases & Growth Factor Gene Expression,* Tissue Engineering, 6 (5), 539–554, Oct. 2000.

* cited by examiner

PROCESSES FOR MAKING CRYOPRESERVED COMPOSITE LIVING CONSTRUCTS AND PRODUCTS RESULTING THEREFROM

This application claims the benefit of Provisional Application No. 60/258,009, filed Dec. 27, 2000.

FIELD OF THE INVENTION

The present invention relates to cryopreserved Composite Living Constructs (CCLCs) which are comprised of separated layers of cultured fibroblasts and cultured keratinocytes and to processes for making CCLCs. The CCLCs are prepared from composite living constructs (CLCs) by equilibrating with cryoprotectant solutions, freezing, and storing at cryogenic temperatures. Prior to use, they are thawed and rinsed to substantially remove the cryoprotectants.

BACKGROUND

CLCs are biologically active composite living constructs that are useful as wound dressings some of which comprise both a fibroblast dermal layer and an epidermal layer of keratinocytes usually on and/or in a matrix. CLCs may be employed for and aid in the regeneration of tissue in wounds that are denuded of skin such as granulating wounds, injuries such as those found in abrasions, excisions, burns and dystrophic epidermolysis bullosa and in ischemic skin such as that present in individuals suffering from decubitus, diabetic, and venous stasis ulcers.

The viability of CLCs as well as those of other cell constructs, such as skin equivalents, grafts, vessels, organs, etc., is short-lived unless such constructs are cryopreserved. Stability of stored cells and constructs are typically limited to about 24 to 120 hours unless they are protected from deterioration by some means such as cryopreservation. A primary goal of cryopreservation is to extend the storage stability of the CLCs without substantially compromising viability and metabolic activity as well as to permit them to maintain such viability and resume metabolic activity upon thawing and rinsing. "Storage stability" is the total time that a CCLC can be stored while minimally compromising viability and metabolic activity upon thawing and rinsing. Long storage stability is important for transplants or implants to be practical and commercially useful, to accommodate shipping and storage schedules, and to maintain sustainable inventories. Measurements useful in assessing the quality of the CCLC that is achieved by cryopreservation are: "construct cell density", the total number of viable cells per unit area; "cell viability", the percent of the total number of cells that are viable; and "metabolic activity", a measure of the overall vigor of the viable cells in terms of their ability to metabolize nutrients and perform other cell maintenance functions. Additional measurements that may be applied to this invention are histologic examination of the structure of the CCLC for the presence, configuration, and distribution of cells within and on the construct, and the ability of the cells and constructs to express wound-healing and tissue regeneration promoters such as growth factors and cytokines.

Cryopreservation typically uses cryoprotectant solutions that comprise a buffered solution containing a non-cell-penetrating component, such as polysaccharides and glycosaminoglyans, e.g. dextran and chondroitin sulfate; and a cell-penetrating component; e.g., glycerol and dimethyl sulfoxide. It is suggested that the role of the cell-penetrating component is to limit cell-disrupting ice crystal formation and to limit destructive dehydration of the intracellular fluid; and that the role of the non-cell-penetrating component is to help maintain the physical integrity and architecture of the CLC.

It should be noted that the very processes of freezing and subsequent thawing inevitably cause a certain amount of cell loss and deterioration in cell viability and metabolic activity. This is due, in part, to the concentration and toxicity of the cryprotectants and the thermal shock and physical damages incurred during freezing and thawing. Thus, it is of importance to sustain the viability and metabolic activity of the thawed and rinsed product as closely as possible to that existing before cryopreservation.

Optimal formulation of cryoprotectants and conditions for crypreservation and for thawing and rinsing are dictated by the CLCs that are to be cryopreserved. The same cryopreservation approach cannot be applied to all CLCs. Formulations and process conditions depend on such factors as: cell type, construct configuration, mass, density, permeability and thickness. Such formulations and conditions include, for cryopreservation and long-term storage, the composition and program of addition and agitation of cryoprotectant solution and the freezing program and storage temperature. They additionally include, for preparation for use in humans and animals, requirements such as a thawing program and the composition of the rinse solution and a rinsing process.

SUMMARY OF THE INVENTION

This invention describes processes for cryopreserving such CLCs, and storing, thawing and rinsing such constructs to yield CCLCs that may, for example, be used to treat wounds in humans and animals. The CLCs employed in the processes of this invention are preferably comprised of separated cultured layers of human fibroblasts on and within a collagen sponge layer and human keratinocytes on a collagen layer that is semipermeable in that it is nonporous to biological cells and permeable to gases and to noncellular components. Such CLCs are described in U.S. Pat. Nos. 5,282,859, RE 35,399 and 6,039,859, to Eisenberg, the entire disclosures of which are incorporated herein by reference. Such CLCs are used, for example, as biologically active dressings for the treatment of acute and chronic skin wounds. The CLCs described in the foregoing Reissue Patent which are useful as starting CLCs in the present invention are composites comprising:

a) a porous sponge first layer comprising a cross-linked collagen sponge, said first layer having upper and lower surfaces, said sponge containing cultured fibroblast cells therein, b) a non-porous to cells, semipermeable second layer, which may or may not be in gel form, comprising a high purity collagen essentially free of exogenous glycosaminoglycans, said second layer having upper and lower surfaces, the lower surface thereof being in contact with the upper surface of said first layer, and c) a layer comprising cultured keratinocyte cells in contact with the upper surface of said non-porous collagen second layer.

A collagen composite matrix useful as the structure for the fibroblasts and keratinocytes is described in claim 1 of U.S. Pat. No. 6,039,760 as follows:

A composite which comprises relative to a horizontal plane:

a) a first layer comprising a collagen matrix having upper and lower surfaces, said matrix being capable of permitting the growth of fibroblast cells therein, and being essentially non-contractible, and b) a non-porous to cells, semipermeable second layer essentially free of exogenous glycosaminoglycans, said layer comprising a non-porous collagen layer having upper and lower surfaces, the lower surface thereof being in contact with the upper surface of said first layer, and being sufficiently non-porous to be capable of maintaining on its surface keratinocyte cells without the substantial invasion of said cells into said collagen matrix.

Other CLCs may also be used as the starting materials in the cryopreservation process of the present invention. The process of the present invention is suitable for fibroblasts on or in any biocompatible absorbable porous material and keratinocytes on any biocompatible absorbent material. Such materials as collagen/GAG, crosslinked gelatin, alginates, synthetic absorbable polymers, such as polyglycolic acid, polycaprolactone co-polymers, and the like may be used.

It is an object of this invention to provide processes for making CCLCs having extended storage stability as well as acceptable cell viability, metabolic activity and structural integrity, compared to that of the corresponding CLC before cryopreservation.

A further object of this invention is to provide processes for making thawed and rinsed CCLCs having an acceptable cell viability, metabolic activity and structural integrity to be useful in treating wounds in humans and animals, compared to that of the corresponding CLCs before cryopreservation.

Still further objects of this invention are to provide CCLCs and thawed and rinsed CCLCs that result from the aforementioned processes.

Thus, embodiments of this invention encompass both the processes and the products therefrom that meet the foregoing objects.

One preferred embodiment of this invention provides a process for making a CCLC comprised of separated layers of cultured fibroblasts and keratinocytes, wherein the CCLC has a cell viability (i.e. the percent of total number of cultured fibroblasts and keratinocytes that are viable) of at least about 70% of the original and wherein the CCLC has a storage stability of at least about 6–12 months.

The CCLCs made by the processes of this invention comprise the following additional characteristics when compared with those of the CLC before cryopreservation: a total number of fibroblasts and keratinocytes which is at least about 50% of the original, a metabolic activity of the viable cells which is at least about 50% of the original cells, and a retention of structural integrity of the matrix.

The process of the invention comprises the steps of: providing a CLC; equilibrating the CLC according to an equilibration program with a cryoprotectant solution comprising at least a non-cell penetrating component such as a polysaccharide or glycosaminoglycans, for example, dextran or chondroitin sulfate and preferably chondroitin sulfate and a cell-penetrating component such as glycerol or dimethyl sulfoxide and preferably dimethyl sulfoxide; lowering the temperature, according to a program, from about ambient temperature to about −90° C.; and storing the CCLC at or below about −150° C. The starting CLC which is subjected to the cryopreservation process of the present invention may be any CLC produced in any number of processes and of any composition provided it contains cells associated with a matrix which are to be cryopreserved. We prefer to use as the CLC starting material the composite prepared according to description in Eisenberg U.S. Pat. No. 5,282, 859. In such a case, the invention contemplates providing a collagen matrix preferably comprised of a collagen sponge layer and a nonporous-to-cell, semipermeable collagen layer and seeding and culturing, in the presence of a cell growth medium, the fibroblasts on and within the collagen sponge and keratinocytes on the nonporous-to-cells, semipermeable collagen layer, thereby providing a CLC. Suitable results are obtained on CLCs about 6–7 cm per side and about 1–3 mm thick.

In the present invention, the CLCs are usually allowed to equilibrate with the cryoprotectant solutions at about ambient temperature after which the temperature is lowered at a rate optimal for the CLCs to slow or halt their cell metabolic activity and to achieve protection against dehydration while minimizing concomitant ice crystal formation. The temperature is lowered further to essentially halt metabolic activity, for long-term storage, to below about −150° C. Thawing, usually to ambient temperature, is followed by rinsing the CCLC to substantially reduce cryoprotectant levels.

The equilibration program comprises the steps of: adding to the CLC a first solution containing the non-cell penetrating component, preferably chondroitin sulfate, at a basal concentration to form an initial equilibrated CLC (suitably between 2–3%), adding to the initial equilibrated CLC a second solution containing the cell-penetrating component, preferably dimethyl sulfoxide at an initial dimethyl sulfoxide concentration of about 20% (suitably between 18–22%) and containing chondroitin sulfate at the same basal concentration as in the first solution to form the final equilibrated CLC in which the chondroitin sulfate is maintained at the original chondroitin sulfate concentration and the dimethyl sulfoxide is brought to a final dimethyl sulfoxide concentration, preferably around 10% (suitably between 9–11%).

A second preferred embodiment of this invention provides a process for making a thawed and rinsed CCLC that may be used to treat wounds in humans and animals. The process for making a thawed and rinsed CCLC comprises, in addition to those given for making the CCLC, the steps of: warming the CCLC from the cold storage temperature to a first higher temperature of about −100° C. by allowing it to stand at room temperature and then further warming the CCLC to a second higher temperature above 0° C. (4° C. to room temperature is suitable) by warming in room temperature saline or water and then rinsing the CCLC substantially free of cryoprotectants.

DESCRIPTION OF THE DRAWINGS

The embodiments and advantages of the present invention will become readily apparent from the detailed description of the invention with reference to the following figures.

DETAILED DESCRIPTION OF THE INVENTION

Figure 1:
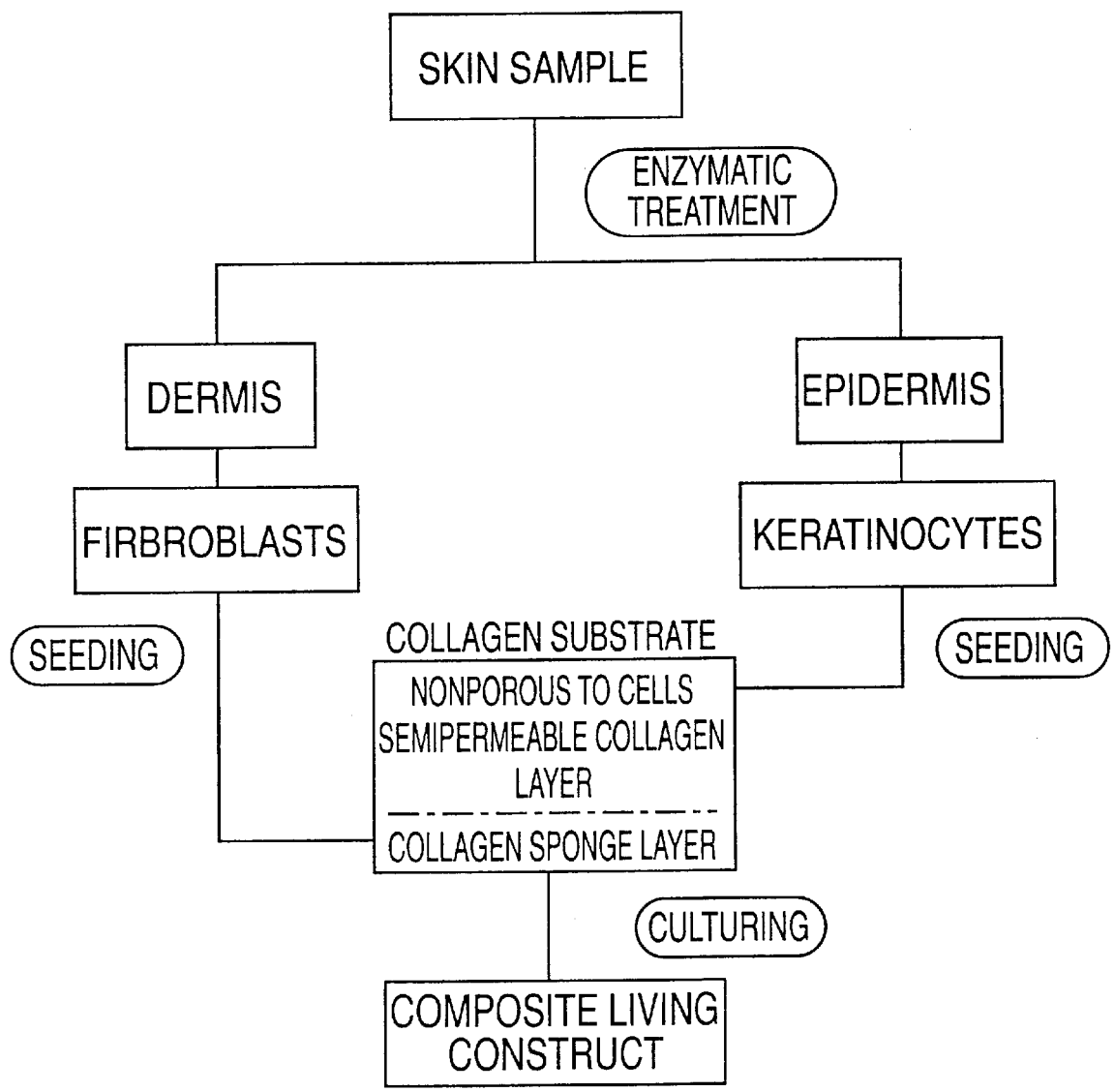
FIG. 1 is a flow scheme of the process for making the CLC used in this invention.

The process for making the preferred CLC, which is to be cryopreserved by the methods of this invention, is herein briefly described with reference to a flow scheme of the process, FIG. 1. The process has been described in detail in U.S. Pat. Nos. 5,282,859, RE 35,399 and 6,039,859, to Eisenberg, which are entirely incorporated herein by reference. The process for making the CLC as described more fully therein and used in this invention comprises: treating a skin sample enzymatically to separate epidermis from dermis; treating the epidermis enzymatically, preferably with trypsin, to release the keratinocyte cells; treating the dermis enzymatically, preferably with collagenase, to release the fibroblast cells. One surface of a crosslinked collagen sponge is coated with a layer of high purity nonporous-to-cells, semipermeable collagen, to form a layered collagen substrate; seeding, i.e. inoculating, the porous, crosslinked collagen sponge with fibroblasts; culturing, i.e., incubating, the seeded collagen sponge in the presence of growth medium to allow growth of the fibroblast cells on and within the collagen sponge; seeding the coated side of the collagen sponge with keratinocytes and culturing in presence of growth medium to yield a CLC comprising a collagen matrix with fibroblasts and keratinocytes.

Various media are used in this invention for operations such as culturing the skin-derived fibroblasts and keratinocytes, seeding and culturing the fibroblasts and keratinocytes, respectively, onto the collagen sponge and the nonporous-to-cells, semipermeable layer of the collagen substrate, and for further culturing of the construct to the point at which it is ready for cryopreservation. Such media comprise Dulbecco's Modified Eagle's Medium (DMEM), well-known to those skilled in the art, and supplements such as growth factors and other nutrient components. The preferred growth medium for the culturing of the CLC used in this invention, is "complete DMEM" (cDMEM) (see Solution A) which contains, in addition to DMEM, components such as fetal bovine serum, recombinant human epidermal growth factor, hydrocortisone, L-glutamine, cholera toxin, nonessential amino acids (NEAA), HEPES (a buffer) and glucose, preferably at a concentration of about 4 g/l. After use, the growth medium (the conditional or spent medium) is removed and fresh growth medium is added periodically during culturing. A preferred medium for rinsing at the end of culturing is DMEM+2 (see Solution B), that is, DMEM plus L-glutamine plus non-essential amino acids (NEAA).

Figure 2:
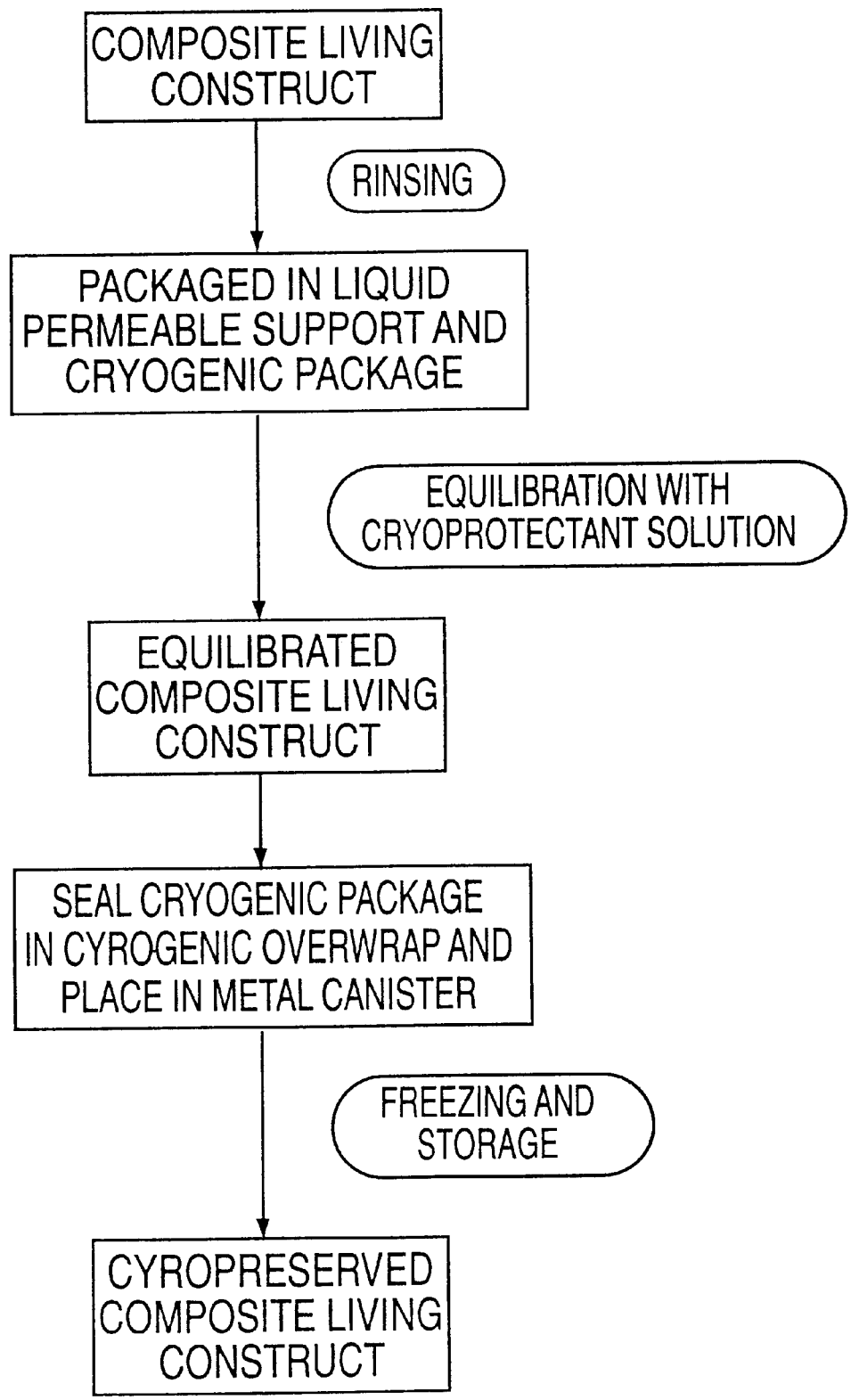
FIG. 2 is a flow scheme of the process for making the CCLCs of this invention.

The process for making the CCLC of this invention comprises: equilibrating the CLC according to an equilibration program with a cryoprotectant solution comprising at least chondroitin sulfate and dimethyl sulfoxide as previously noted; lowering the temperature, according to a temperature lowering program, from about ambient temperature to at least about −90° C. and storing at a temperature below about −150° C. It should be noted that details given in the following discussion are meant to serve as examples of how, in general and in preferred modes, the various steps of the processes are carried out and to describe examples of products that result from such processes and are not meant to exclude alternative methods that may logically be used, and the products resulting therefrom, by those skilled in the art who might practice this invention. The following immediate discussion is given with reference to FIG. 2, a flow scheme of the process for making the CCLC of this invention.

Preparation of the CCLC

The Solutions

Solution A

| cDMEM(hg) | | |
|---|---|---|
| Component | Conc. | |
| FBS | 10% | v/v |
| L-glutamine | 5.98E + 00 | mM |
| rhEGF | 3.04E − 02 | ug/ml |
| HC | 4.01E − 01 | ug/ml |
| CT | 9.69E − 10 | mM |
| 1M HEPES | 3.07E − 03 | M |
| 1N NaOH | 1.00E − 03 | N |
| 45% glucose | 2.98E + 00 | g/L |
| L-alanine | 100.2 | uM |
| L-Asparagine.H2O | 100.2 | uM |
| L-Aspartic acid | 100.2 | uM |
| L-glutamic acid | 100.2 | uM |
| Glycine | 100.2 | uM |
| L-proline | 100.2 | uM |
| L-serine | 100.2 | uM |
| DMEM | | |

Solution B

| DMEM + 2 | | | |
|---|---|---|---|
| | Component | | |
| | L-Glutamine | 5.8 | uM |
| NEAA | L-alanine | 96.2 | uM |
| NEAA | L-Asparagine.H2O | 96.2 | uM |
| NEAA | L-Aspartic acid | 96.2 | uM |
| NEAA | L-glutamic acid | 96.2 | uM |
| NEAA | Glycine | 96.2 | uM |
| NEAA | L-proline | 96.2 | uM |
| NEAA | L-serine | 96.2 | uM |
| | DMEM | | |

Solution C

| Primary Cryo Solution | | |
|---|---|---|
| Component | | |
| 1M HEPES | 2.50E − 02 | M |
| Sodium Biocarbonate, 7.5% | 2.00E − 03 | w/v |
| Folic Acid | 4.00E − 03 | mg/ml |
| L-glutamine | 4.0 | mM |
| 1M Sodium Hydroxide | 4.40E − 03 | M |
| Chondroitin Sulfate | 2.50E − 02 | w/v |
| DMEM | | |

Solution D

| Secondary Cryo Solution |
|---|
| primary Cryo solution+ 20% v/v DMSO |

1. Removal of Protein-Containing Growth Medium

The CLC described above is rinsed with a protein-free DMEM+2 (Solution B) to remove conditioned medium, agitated, and then incubated for a period of time, e.g., about 30 minutes. The DMEM+2 in contact with the CLC is then replaced with fresh DMEM+2 and agitated. This procedure is repeated, preferably at least about two more times. The CLC is then incubated in DMEM+2, preferably for less then eight hours, until it can be placed in a primary package preparatory to cryopreservation.

2. Primary Packaging

The rinsed CLC is removed from incubation and is placed in a liquid permeable tray between layers of medical grade nonadherent polyethylene net or medical grade gauze. The CLC, in its support, is placed within a cryogenically compatible package, the package being fitted with fluid access and removal means. The first cryogenically compatible package, now containing the CLC within the support, is sealed by means such as heat.

3. Equilibration of CLC with Cryoprotectant solutions

Two solutions are prepared in low bicarbonate DMEM (LB-DMEM) comprising DMEM, folic acid, L-glutamine, sodium bicarbonate, NaOH and HEPES. The first solution (Solution C) is the primary cryoprotectant solution comprising chondroitin sulfate at a basal concentration of about 2.5% with a suitable range of about 2–3%. The second cryoprotectant solution (Solution D) comprising an approximately 4:1 mixture of the primary solution and dimethyl sulfoxide. The solutions are preferably prepared and then stored at temperatures below room temperature to help dissipate the heat of solution formed during the preparation. Once prepared, the cryoprotectant solutions are preferably used at room temperature.

The primary cryoprotectant solution is admitted through the fluid access means to the package, preferably by a pumping means, while the package is being agitated by means such as a shaking platform, to form an initial equilibrated CLC. Any non-contaminating pumping means may be used such as a peristaltic pump. The temperature of the primary cryoprotectant solution is introduced into the package at between 5–20° C., preferably at room temperature.

The secondary cryoprotectant solution (Solution D) then is admitted through the fluid access means to the package with agitation, in a manner similar to that used for the primary cryoprotectant solution, to form the final equilibrated CLC, said CLC having a chondroitin sulfate concentration of about 2.5% and dimethyl sulfoxide concentration of about 10%. The secondary cryoprotectant solution admitted to the package is between about 5–20° C., preferably at room temperature.

Residual air and excess cryoprotectant solution is withdrawn from the package by pumping means, preferably by a peristaltic pump. All fluid access means then are closed or otherwise sealed, e.g., heat sealing and removed.

4. Freezing and Storage of Cryo-Equilibrated CLC (CeCLC)

The package containing the CeCLC is sealed, e.g., by thermal or ultrasonic means, and placed within a cryogenically compatible overwrap to provide a double-packaged CLC which is then placed in a heat-conducting, e.g. metal, preferably aluminum, canister. The temperature of the double-packaged CLC then is lowered preferably using the vapor phase of liquid nitrogen according to a temperature lowering program. The temperature lowering program may be implemented by means of microprocessor-controlled freezing chambers. A temperature probe is employed to monitor the temperature of the freezing chamber and a second probe monitors the surface of the CLC. In practice, it is preferred to monitor the temperature in the ambient space around the CLC with the vapor phase of the liquid nitrogen as opposed to the temperature of the CLC itself. Thus, the temperature recited in the freezing programs herein is that in the freezing chamber unless otherwise stated.

The preferred temperature lowering program comprises the steps of: lowering the temperature from ambient temperature to about 4° C.; lowering the temperature from about 4° C. to about −20° C. at a rate of about 1° C./minute and holding the temperature at about −20° C. for about 15 minutes; lowering the temperature from about −20° C. to about −25° C. at a rate of about 0.5° C./minute and holding the temperature at about −25° C. for about 15 minutes; lowering the temperature from about −25° C. to about −70° C. at a rate of about 1° C./minute; and lowering the temperature from about −70° C. to about −90° C. at a rate of about 5° C./minute. At this point, it is preferred to hold the temperature of the freezing chamber at about −90° C. until the temperature at the CLC surface is between about −85° C. to −90° C. The CCLC is then stored below about −150° C. and preferably at about −170° C. to −190° C. in the vapor phase of liquid nitrogen.

5. Thawing and Rinsing of CCLC

Figure 3:
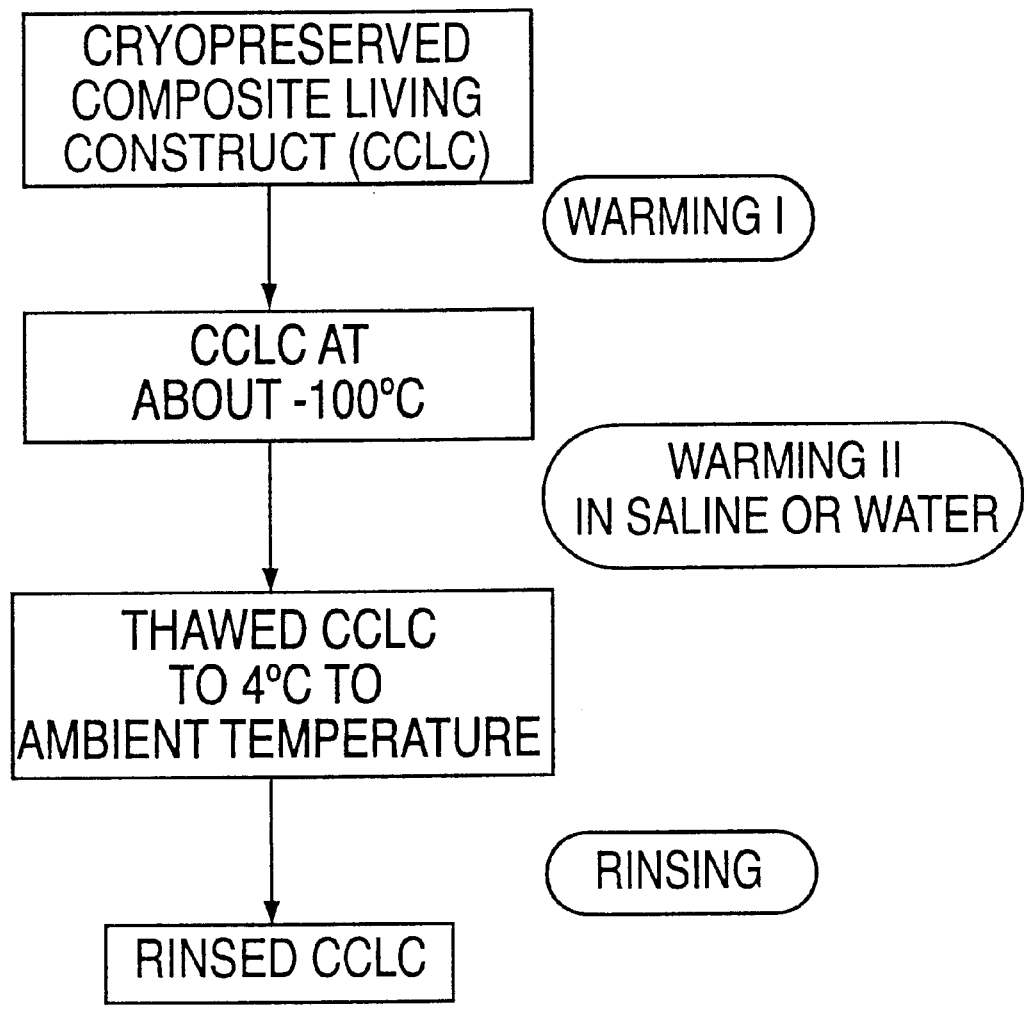
FIG. 3 is a flow scheme of the process for making a thawed and rinsed CCLC of this invention.

FIG. 3 depicts a flow scheme of the processes for thawing and rinsing the CCLC of this invention. The process comprises two steps, the first of which is to allow the frozen CCLC to warm up to about −100° C. by allowing it to stand at room temperature. The second step involves thawing the frozen CCLC to a temperature above freezing by warming it in room temperature saline or water and thereafter rinsing the CCLC substantially free of cryoprotectants.

In practice, the double-packaged CCLC is removed from vapor phase liquid nitrogen storage in the metal canister and permitted to warm for about four minutes at about ambient temperature, to the first higher temperature usually about −100° C. The double-packaged CCLC is further warmed for about five minutes in about ambient temperature water or saline to the second higher temperature, which is in the range from about 4° C. to about ambient temperature.

The CCLC is removed from its outer package and transferred to the sterile or clean field. The CCLC is then removed from the primary package while in its liquid permeable support, placed in normal saline at about ambient temperature, with agitation, for about ten minutes, thereby rinsing it to substantially remove the cryoprotectants. Alternatively, the rinsing step may be performed in two or more steps by removing the saline rinse solution after five minutes or so of agitation and replacing it with fresh saline and repeating the agitation for another five minutes or less.

Assays of in Vitro Function

The following in vitro assays are used to assess the immediate and long-term effects of cryopreservation, thawing and rinsing processes on CCLC. The assays include cryoprotectant residuals, cell number, percent cell viability, metabolic activity, histologic examination and cytokine expression. Samples for assaying CCLC are taken using appropriately sized diameter biopsy punches selected randomly from the CCLC device.

Cell Number and Cell Viability

Biopsy punch samples taken from the CLC or the CCLC are enzymatically digested to release fibroblasts and keratinocytes from the collagen matrix. The percent cell viability and cell number are then determined by a Hemocytometer using Trypan Blue dye exclusion to differentiate living from dead cells.

Metabolic Activity

Metabolic activity is a measure of the overall physiologic state of viable cells. Biopsy punch samples, taken from the CLC or the CCLC, are incubated with Alamar Blue dye. The assay measures mitochondrial activity using a non-cytotoxic Alamar Blue dye which diffuses into the cell mitochondria and undergoes a reduction-oxidation reaction to give a fluorescent product that is read by a fluorescent spectrophotometer.

Histology

Histology provides the following visual assessment of the structure and morphology of both the CLC and CCLC: 1. presence and distribution of fibroblasts and keratinocytes within and on the matrix of the collagen substrate. 2. morphology of the matrix itself, such as the effects of cryopreservation or thawing on the attachment and distribution of keratinocyte cells on the nonporous-to-cells, semipermeable collagen layer, the attachment and distribution of fibroblast cells on and within the collagen sponge layer and 3. the structural integrity and morphology of the CCLC scaffold.

Cytokines

The expression of cytokines is a measure of the potential of CCLC to stimulate wound healing and tissue regeneration. Cytokine expression data is obtained by analyzing spent culture media of the CLC prior to cryopreservation and after thawing, rinsing and incubation for about 48 hours in CDMGM-hG. The spent media are assayed for cytokines using appropriate available ELISA kits.

TABLE 1 compares the in vitro functions of the CCLC and the CLC before cryopreservation, in terms of the values obtained for cell number, cell viability and metabolic activity, in support of the objectives and the claims of this invention.

TABLE 2 compares the expression of various cytokines by CLC before cryopreservation and by CCLC, in their incubation media, after about 48 hours of incubation.

Histological Studies

Figure 4A:
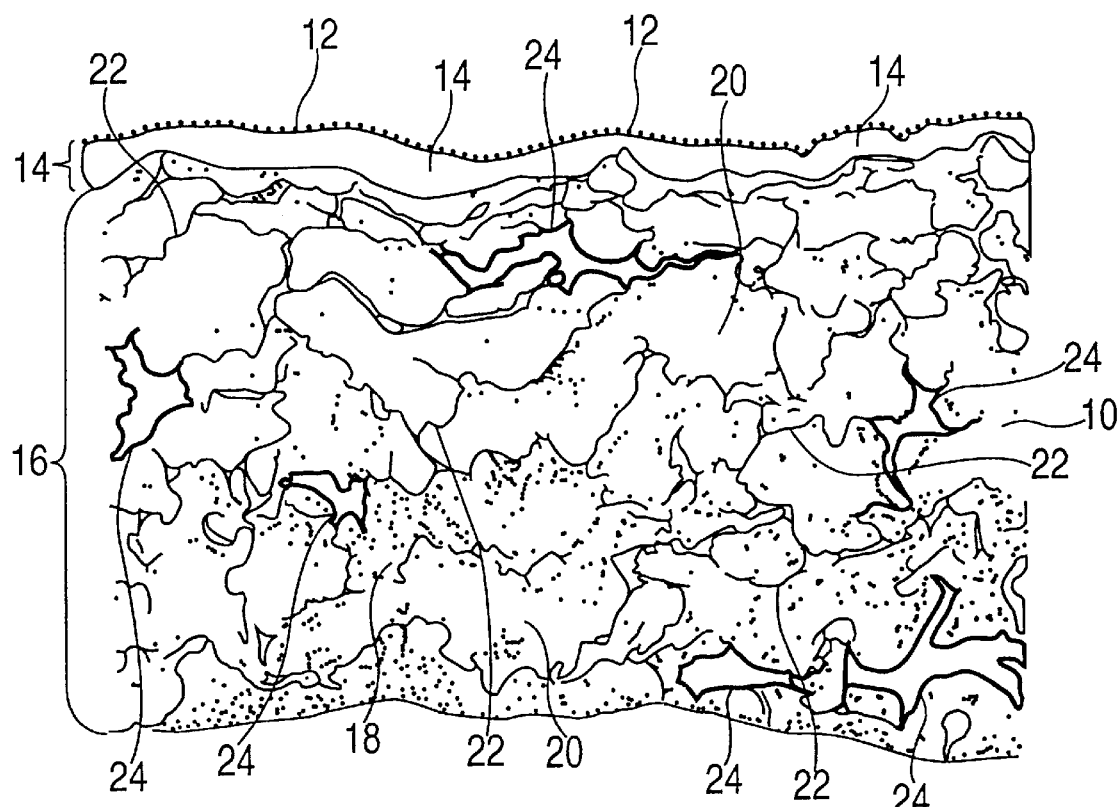
FIG. 4 shows a histological cross-section of a freshly made CLC (4a) used in this invention and a CCLC (4b) of this invention each showing a normal human keratinocyte cells layer (4a) of a CLC used in this invention, just before cryopreservation, with the keratinocytes of a CCLC (4b) of this invention after cryopreservation and normal human fibroblast cells layer of a CLC used in this invention (4a), just before cryopreservation, with those of a CCLC (4b) of this invention after cryopreservation.

FIGS. 4a) and 4b) are pictorial representations of cross-sectional histological views of the CLC 10 used in this invention before cryopreservation and CCLC 100 obtained from CLC 10 after cryopreservation. The two pictures show regions of reference before and after cryopreservation according to the invention. The CLC of FIG. 4a), beginning from the top of the figure has a nonporous-to-cells, semipermeable collagen layer 14 having normal human keratinocytes 12 on the semipermeable collagen layer 14, a collagen sponge layer 16 in which spaces 20 are open air spaces of the sponge layer some of which contain normal human fibroblasts 18 within the spaces 20. Boundary lines 22 are the collagen structure of the collagen sponge layer 16 while the thinner boundary lines 24 surround thicker areas of the collagen structure.

Figure 4B:
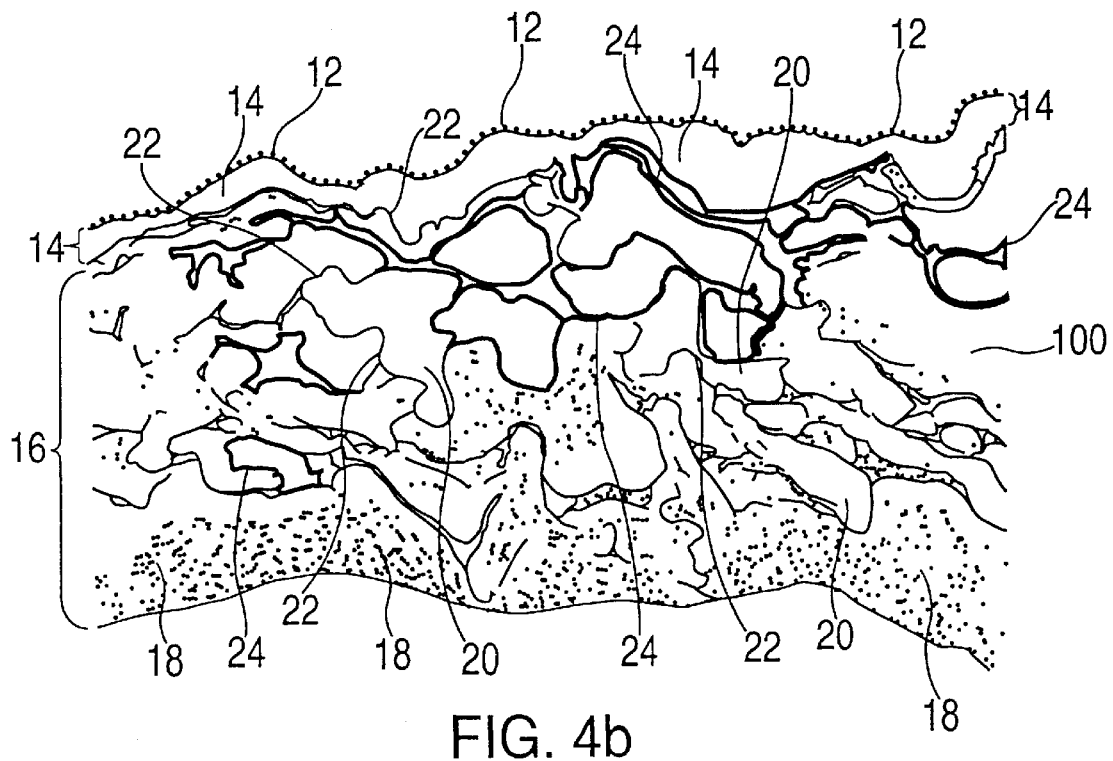

CCLC 100 (FIG. 4b) after cryopreservation has the same sequence of layers and cells top to bottom as is shown in FIG. 4a).

In all instances the comparison between the various components of the CLC and the CCLC (i.e., before and after cryopreservation) shows that there is little or no difference in morphologies of the collagen sponge layer 16 and the semipermeable collagen layer 14, the keratinocytes 12 and the presence and distribution of fibroblasts 18 within the matrix of the collagen sponge 16, attachment and distribution of keratinocytes 12 on the nonporous-to-cells, semipermeable layer of collagen 14, and the structural integrity of the boundaries 22 and 24 of the CCLC 100 and CLC 10.

The following examples illustrate specific embodiments of the present invention.

EXAMPLE 1

The following procedure was conducted under aseptic and, unless otherwise noted, ambient conditions:

CLCs measuring approximately 6 cm×6 cm×2–3 mm, were produced as described in the Eisenberg U.S. Pat. Nos. 6,039,760, 5,282,859, and Reissue No. 35,399 with the following exceptions: a high glucose culture medium containing about 4 g/L glucose (instead of 1 g/L) was used with a feeding schedule for exchanging spent medium with fresh medium of every 2–3 days for up to 11–13 days as desired instead of the 14 days described in the patents. During the last 3 days of culture (maturation period), spent medium samples were collected and frozen in aliquots and held for testing for expression of various cytokines using commercially available ELISA assays. On one of the last three days of culturing, the CLCs were rinsed in protein-free, serum-free medium and all but one subjected to the cryopreservation step below. The one saved unit was tested for cell number and viability, metabolic activity, and histology testing to be compared with the same parameters for the CCLCs prepared below.

TABLE 1

Comparative Results for in vitro Functions of CCLC and CLC

|  | Number of Samples | Average ± Std Dev. (×10$^{-5}$/cm$^2$) | CCLC/CLC (%) |
|---|---|---|---|
|  |  | Cell Number |  |
| CCLC | 30 | 10.47 ± 2.06 | 72.96 |
| CLC | 28 | 14.35 ± 2.59 |  |

|  | Number of Samples | Average ± Std Dev. (%) | CCLC/CLC (%) |
|---|---|---|---|
|  |  | Cell Viability |  |
| CCLC | 30 | 95.53 ± 1.83 | 98.67 |
| CLC | 28 | 96.82 ± 1.56 |  |
|  |  | Metabolic Activity |  |
| CCLC | 30 | 15.87 ± 3.24 | 83.05 |
| CLC | 28 | 19.11 ± 5.02 |  |

TABLE 2

Cytokine Expression by Thawed and Rinsed CCLC and by CLC

|  | bFGF | GM-CSF | IL-1α | KGF (pg/cm$^2$/day) | VEGF | M-CSF |
|---|---|---|---|---|---|---|
| CCLC |  |  |  |  |  |  |
| Ave ± Std Dev | 128 ± 11 | 6837 | 104 ± 49 | 687 ± 19 | 3353 ± 579 | 530 ± 180 |
| CLC |  |  |  |  |  |  |
| Ave ± Std Dev | 14 ± 7 | 2908 ± 1408 | 8 ± 3 | 291 ± 95 | 5350 ± 240 | 986 ± 62 |

Each rinsed CLC was placed in a liquid permeable tray between two opposing sheets of non-adherent medical grade gauze in such a way that the 6×6 cm surfaces of the CLC were accessible for subsequent treatment by a cryoprotectant solution. The tray was then placed into and heat-sealed within a cryogenic bag having luer lock connectors. The cryogenic bags were then connected to a peristaltic pump via the luerlock connectors and the pump operated to withdraw air from the bags. A primary cryoprotectant solution of 75 cc volume (Solution C) at or below room temperature containing 2.5% chondroitin sulfate was then introduced using the pump as the bags were continuously agitated. After 9–11 minutes of equilibration at room temperature with cyroprotectant Solution C under agitation, 75 cc of a secondary cryoprotectant solution (Solution D) containing 20% DMSO and 2.5% chondroitin sulfate at or below room temperature was introduced using the pump with constant agitation. After a total of 12–13 minutes, the pump was reversed, first to withdraw any excess air and then to withdraw 100 cc of solution. The solution introduction ports then were heat-sealed and excess tubing trimmed. Each sealed package was then placed into a separate cryogenic overwrap package which then was vacuum heat-sealed. The double-packaged units were then placed into aluminum canisters and placed into a microprocessor-controlled rate freezing chamber. The units were frozen under a microprocessor controlled schedule using the vapor phase of liquid nitrogen and then stored in the vapor phase of liquid nitrogen at below −150° C. until ready for use. The temperature lowering program comprised the steps of: lowering the chamber temperature from ambient temperature to about 4° C.; lowering the chamber temperature from about 4° C. to about −20° C., at a rate of about 1° C./minute and holding the chamber temperature at about −20° C. for about 15 minutes; lowering the chamber temperature from about −20° C. to about −25° C., at a rate of about 0.5° C./minute and holding the chamber temperature at about −25° C. for about 15 minutes; lowering the chamber temperature from about −25° C. to about −70° C. at a rate of about 1° C./minute; lowering the chamber temperature from about −70° C. to about −90° C. at a rate of about 5° C./minute; holding the CLC in the freezing chamber until the surface of the CLC reached −85° C. to −90° C.; and storing the CCLC below about −150° C.

The cryopreserved (CCLC) units prepared above are suitable for either patient grafting or other studies after subjecting thereto the following procedures. First, the CCLC is warmed at room temperature for about four minutes. At the end of the warming time, the overwrapped packaged CCLC is placed into 4 liters of room temperature sterile water (or sterile saline) bath for thawing in the second stage for about five to seven minutes with periodic manual agitation. The overwrap is cut open, the inner package removed and cut open, and the tray containing the CCLC removed. The CCLC in the tray is rinsed to remove the cryoprotectant solution by placing it into 3 liters of sterile saline, and agitating for about ten minutes, or alternatively, for five minutes after which the saline is removed and replaced with another 3 liters of saline and agitating for another five minutes. At the end of that time, the CCLC can be removed from the tray and applied onto a patient or used for in vitro studies.

For in vitro studies, the CCLC can be placed back into the high glucose culture medium and incubated and assayed for cytokine expression using commercially available ELISA kits. The CCLC can also be used immediately for testing, as was done in the pre-cryopreservation step, that is, tested for cell number, viability, metabolic activity, and histology, and testing for comparison with the pre-cryopreservation material.

EXAMPLE 2

SCID Mouse Grafting

An in vivo grafting study was performed to compare the healing characteristics of full-thickness skin wounds in Severe Combined Immuno-Deficient (SCID) mice grafted with the CCLC of Example 1 compared to a fresh CLC prepared according to the Eisenberg U.S. Patents referred to in Example 1 and used without being subjected to cryopreservation and/or freezing. The study was conducted as two trials of twelve animals each, which were initiated approximately 24 hours apart. A full-thickness wound (1.7 cm in diameter) was created using surgical scissors on the dorsum of each mouse just prior to applying a CLC or CCLC graft of the same size and shape into the wound. Six mice in each trial received fresh CLC grafts and six mice received CCLC grafts. Samples of CLC and CCLC from each of the four groups were assayed in vitro for cell yield, cell viability, and the ability to secrete several wound-healing associated cytokines and growth factors. Following placement of the grafts, the wounds were covered with one layer of polyethylene net, then with two layers of paraffin gauze and three circuits of dressing around the trunk of each mouse to secure the grafts.

Mice were observed and weighed daily. Bandages were removed and wounds were examined and photographed macroscopically 8 and 14 days after grafting. The degree of wound contraction was calculated on day 8 and 14. On day 14, the mice were sacrificed and the wounds were excised for histological preparation and evaluation. All biopsy samples were placed in fixative, sectioned at 8 um and stained with hematoxylin and eosin, and/or trichrome and/or orcein and methylene blue. The extent of epithelialization, the average dermal and epidermal thickness and the cellularity of the dermis were calculated. Other histological features were noted as comments.

No significant adverse effects were observed during the course of this study. By day 14, most of the grafts were not apparent due to the healing processes and resorption of the collagen matrix of the CLC and CCLS. The fresh CLC and CCLC grafts produced similar results with respect to macroscopic wound appearance and contraction. Microscopically, no significant differences were noted in the healing properties of wounds treated with fresh CLC or CCLC grafts. By day 14, 8/12 and 7/12 of the wounds in the fresh CLC and CCLC groups, respectively, had undergone complete epithelialization. No difference in epithelialization was observed between fresh CLC and CCLC grafts and it was concluded, from the results of this study, that CCLC grafts of the invention and fresh CLC were not substantially different and had similar effects on wound healing parameters when compared in a full-thickness would healing model in SCID mice.

We claim:

1. In the method for the cryopreservation of fibroblast cells and keratinocyte cells present in a matrix holding said cells wherein solutions comprising a non-cell-penetrating component and a cell-penetrating component are used as the cryoprotectant solutions and wherein said cells are equilibrated with said solutions and further wherein the cryoprotectant solution-equilibrated cells are subjected to freezing temperatures in a chamber, the improvement which comprises the steps of a) lowering the temperature from ambient temperature to about 4° C., b) lowering the temperature from about 4° C. to about −20° C. at a rate of about 1° C./minute and holding the temperature at about −20° C. for about 15 minutes, c) lowering the temperature from about −20° C. to about −25° C. at a rate of about 0.5° C./minute and holding the temperature at about −25° C. for about 15 minutes, d) lowering the temperature from about −25° C. to about −70° C. at a rate of about 1° C./minute, e) lowering the temperature from about −70° C. to about −90° C. at a rate of about 5° C./minute, f) storing at a temperature of about −150° C. or below.

2. The method of claim 1 wherein said non-cell-penetrating component is selected from the group consisting of a polysaccharide and glycosaminoglycans and the cell-penetrating component is selected from the group consisting of glycerol and dimethyl sulfoxide and wherein said equilibration takes place at about ambient temperature and further wherein the first step of equilibration comprises adding to said cells a first solution containing the non-cell-penetrating component and allowing the cells to equilibrate therewith followed by adding a second solution comprising the cell-penetrating component and the non-cell penetrating component to said cells and allowing the cells to equilibrate therewith.

3. The method according to claim 2 wherein the non-cell-penetrating component is chondroitin sulfate or dextran and the cell-penetrating component is dimethyl sulfoxide.

4. The method according to claim 3 wherein the first solution comprises chondroitin sulfate at a basal concentration of about 2–3% and wherein the second solution comprises a mixture of the first solution and dimethyl sulfoxide in the approximate ratio of 4:1.

5. The method according to claim 4 wherein the first solution contains approximately 2–3% chondroitin sulfate and after equilibration therewith at room temperature an equal amount of the second solution containing approximately 20% DMSO and 2–3% chondroitin sulfate is introduced and equilibrated therewith.

6. The method according to claim 1 wherein following the chamber temperature lowering step at from about −70° C. to about −90° C., an additional step is performed which comprises holding the temperature of the freezing chamber at approximately −90° C. until the temperature of the matrix surface is between about −85° C. and −90° C. and thereafter storing the matrix at a temperature of about −150° C. or lower.

7. The method according to claim 6 wherein the matrix is stored at approximately −170° C. to −190° C.

8. The method according to claim 6 wherein the temperature lowering steps are is achieved through the use of the vapor phase of liquid nitrogen.

9. The method according to 6 claim wherein the matrix comprises
   a) a sponge first layer comprising a cross-linked collagen sponge, said first layer having upper and lower surfaces, said sponge containing cultured fibroblast cells therein,
   b) a non-porous second layer comprising a high purity collagen essentially free of exogenous glycosaminoglycans, said second layer having upper and lower surfaces, the lower surface thereof being in contact with the upper surface of said first layer, and
   c) a layer comprising cultured keratinocyte cells in contact with the upper surface of said non-porous collagen second layer.

10. The method according to claim 1 wherein the matrix structure comprises a collagen sponge layer containing cultured human fibroblasts and a collagen layer that is semi-permeable and non-porous to biological cells and permeable to gases and non-cellular components upon which a cultured layer of human keratinocytes is present.

* * * * *